United States Patent [19]

Mehra et al.

[11] Patent Number: 4,953,551
[45] Date of Patent: Sep. 4, 1990

[54] METHOD OF DEFIBRILLATING A HEART

[75] Inventors: Rahul Mehra, Stillwater; William Combs, Minneapolis, both of Minn.

[73] Assignee: Medtronic, Inc., Minneapolis, Minn.

[21] Appl. No.: 394,249

[22] Filed: Aug. 7, 1989

Related U.S. Application Data

[63] Continuation of Ser. No. 3,358, Nov. 14, 1987, abandoned.

[51] Int. Cl.$^5$ .............................................. A61N 1/00
[52] U.S. Cl. ......................... 128/419 D; 128/419 PG
[58] Field of Search ............ 128/419 D, 419 PG, 421, 128/784

[56] References Cited

U.S. PATENT DOCUMENTS

| | | | |
|---|---|---|---|
| 2,534,043 | 12/1950 | MacPhail | 128/419 S |
| 3,211,154 | 10/1965 | Becker et al. | 128/421 |
| 3,224,447 | 12/1965 | Becker et al. | 128/421 |
| 3,241,555 | 3/1966 | Caywood et al. | 128/421 |
| 4,010,755 | 3/1977 | Preston | 128/404 |
| 4,026,302 | 5/1977 | Grayzel | 128/418 |
| 4,291,699 | 9/1981 | Geddes et al. | 128/419 D |
| 4,300,567 | 11/1981 | Kolenik et al. | 128/419 D |
| 4,498,478 | 2/1985 | Bourgeois | 128/419 |
| 4,548,203 | 10/1985 | Tacker et al. | 128/419 D |
| 4,595,009 | 6/1986 | Leinders | 128/419 D |
| 4,662,377 | 5/1987 | Heilman et al. | 128/419 D |
| 4,800,883 | 1/1989 | Winstrom | 128/419 |
| 4,825,871 | 5/1989 | Cansell | 128/419 D |

FOREIGN PATENT DOCUMENTS

2070435 9/1981 United Kingdom .
2083363 3/1982 United Kingdom .

OTHER PUBLICATIONS

Schuder, John C. et al., "Defibrillation of 100 kg Calves with Asymmetrical, Bidirectional, Rectangular Pulses", *Cardiovascular Research*, vol. 18, pp. 419–426, 1984.
Wetherbee, Jule N. et al., "Subcutaneous Patch Electrode—A Means to Obviate Thoracotomy for Implantation of the Automatic Implantable Cardioverter Defibrillation System?", *Abstracts Circulation*, vol. 72, Supp. III, p. III-384, Oct. 1985.
Schuder, John C. et al., "A Multielectrode-Time Sequential Laboratory Defibrillator for the Study of Implanted Electrode Systems", *Trans. Amer. Soc. Artif. Int. Organs*, vol. XVIII, pp. 514–519, 1972.
Schuder, John C. et al., "Transthoracic Ventricular Defibrillation in the 100 kg Calf with Symmetrical One-Cycle Bidirectional Rectangular Wave Stimuli", *IEEE Transactions on Biomedical Engineering*, vol. BME-30, No. 7, pp. 415–422, Jul. 1983.
Schuder, John C. et al., "Ultrahigh-Energy Hydrogen Thyraton/SCR Bidirectional Waveform Defibrillator", *Med. & Biol. Eng. & Comput.*, vol. 20, pp. 419–424, Jul. 1982.
Dahlback, O. et al., "Ventricular Defibrillation with Square-Waves", Letters to the Editor, *The Lancet*, vol. 2, pp. 50–51, Jul. 2, 1966.
Schuder, John C. et al., "Transthoracic Ventricular Defibrillation with Square-Wave Stimuli: One-Half Cycle, One Cycle, and Multi-Cycle Waveforms", *Circulation Research*, vol. NV, pp. 258–264, Sep. 1964.
Jones, Janice L. et al., "Decreased Defibrillator-Induced Dysfunction with Biphasic Rectangular Waveforms", *Am. J. Physiology*, 247, (5 Pt. 2), pp. H792–H796, Nov. 1984.

*Primary Examiner*—Francis Jaworski
*Assistant Examiner*—George Manuel
*Attorney, Agent, or Firm*—Joseph F. Breimayer; Reed A. Duthler

[57] ABSTRACT

A method of terminating ventricular fibrillation by the delivery of an asymmetric biphasic current pulse to three separate electrodes. A first catheter mounted electrode is located in the apex of the right ventricle (RV). A second electrode carried on the same catheter is located outside the atrium preferably in the superior vena cava (SV). A third plate electrode is located subcutaneously outside the chest cavity. Preferably, the SVC electrode and the subcutaneous plate electrode are electrically interconnected and an asymmetrical biphasic current pulse is applied between this electrode pair and the RV electrode to defibrillate the heart.

12 Claims, 4 Drawing Sheets

FIG. 4

| exp # | SEQUENTIAL THRESHOLD (MONOPHASIC PULSE) (2 50uF CAPACITORS) | | SIMULTANEOUS THRESHOLD (BIPHASIC ASYMMETRIC PULSE) (1 50uF CAPACITOR) | |
|---|---|---|---|---|
| | VOLTAGE (VOLTS) | STORED ENERGY (JOULES) | VOLTAGE (VOLTS) | STORED ENERGY (JOULES) |
| 1 | 650 | 21.1 | 627 | 9.8 |
| 2 | 581 | 16.9 | 504 | 6.4 |
| 3 | 557 | 15.5 | 445 | 5.0 |
| 4 | 533 | 14.2 | 460 | 5.3 |
| 5 | 654 | 21.4 | 510 | 6.5 |
| 6 | 829 | 34.4 | 563 | 7.9 |
| 7 | 474 | 11.2 | 598 | 8.9 |
| 8 | 607 | 18.4 | 594 | 8.8 |
| 9 | 417 | 8.7 | 416 | 4.3 |
| 10 | 587 | 17.2 | 630 | 9.9 |
| 11 | 610 | 18.6 | 591 | 8.7 |
| 12 | 621 | 19.3 | 649 | 10.5 |
| MEAN | 593 | 18.1 | 549 | 7.7 |
| SD | 102 | 6.4 | 79 | 2.1 |

METHOD OF DEFIBRILLATING A HEART

This is a continuation of copending application(s) Ser. No. 07/003,358 filed on Jan. 14, 1987 now abandoned.

BACKGROUND OF THE INVENTION

This invention relates to the control of cardiac arrhythmias and particularly to terminating fibrillation in the heart. The method uses an improved electrode configuration for use with a single monophasic or biphasic current pulse to effectively lower the energy required to successfully defibrillate the heart.

Ventricular fibrillation is characterized by the random depolarization of individual fibers of the heart which greatly reduces the cardiac output of the heart and leads to death within minutes of onset. Conventional external treatment for fibrillation calls for the application of an electric shock supplied by a pair of paddles across the chest of the patient which simultaneously depolarizes all of the cardiac muscle fibers. This process permits a resynchronization of the ventricular muscle fibers.

Implantable defibrillator systems have been proposed for use in patients susceptible to sudden death syndrome. Traditionally such systems have comprised an implanted pulse generator coupled to a plurality of electrodes located in and around the heart. Such implantation techniques require a thorocotomy to place the electrodes. However, the most fundamental problem associated with implantable defibrillation is the high energy required to successfully defibrillate the heart.

One early attempt to produce an electrode system suitable for use in an automatic implantable defibrillator is illustrated in U.S. Pat. No. 3,942,536. In this system, a single right ventricular endocardial lead is used having one set of electrodes at its distal tip for location in the apex of the right ventricle, and a second set of electrodes spaced from the set of electrodes on the distal tip a sufficient distance to place them outside the heart, in the superior vena cava. Other endocardial ventricular defibrillation lead systems are illustrated in U.S. Pat. No. 3,857,398 issued to Rubin and in U.S. Pat. No. 4,355,646 issued to Kallok.

Experience with these lead systems have shown that the energy required to defibrillate the heart utilizing a single pair of electrodes while significantly less than that required by use of an external defibrillator is still sufficiently large to make construction of a battery powered automatic implantable defibrillator difficult. Additionally, the small electrode areas required by catheter mounted systems have been shown to increase the risk of tissue damage because of the increase current density present at the electrode sites.

In an effort to overcome this problem, electrode systems have been proposed such as that shown in U.S. Pat. No. 4,030,509 to Heilman which shows a collection of large surface area electrodes. One set of electrodes is applied to the apex of the heart, a second set is applied to the atria of the heart. As an alternative, it has been suggested that a superior vena cava electrode on an endocardial lead may also be used in conjunction with the large area electrode applied directly to the apex of the heart. One problem associated with the use of epicardial patches on the heart is that the surgery to attach the electrodes is highly invasive, and therefore undesirable.

Other large surface area electrodes for application to the human heart are disclosed in U.S. Pat. No. 4,291,707 issued to Heilman et al, which discloses electrodes fabricated of metallic mesh, sandwiched between two layers of chemically inert electrically insulative material.

Recently, it has been proposed that rather than delivering electrical energy between electrodes located in the apex of the heart and electrodes located on or in the superior vena cava or atrium of the heart that a return to application of electrical energy transversely across the heart is desirable. For example, in published European Pat. Application Publication No. 0 095 726 by the Purdue Research Foundation, it is proposed that four epicardial mesh electrodes be arranged orthogonally around the heart and that defibrillation be accomplished using two sequential orthogonal defibrillation pulses.

A large portion of the early work on automatic implantable and external defibrillators was performed with stimulators which provided a single monophasic pulse, or a symmetrical biphasic pulse.

In the present invention, a combination of electrode placement and size have been optimized to produce a system capable of defibrillation at lower energies than have been heretofore possible. It appears that the electrode placement achieves sufficient spatial isolation to minimize the risk of myocardial damage. The electrode system also has the major advantage of not requiring a thoracotomy for electrode placement.

The electrode system is used in conjunction with a novel waveform providing a single asymmetric biphasic defibrillation pulse.

SUMMARY OF THE INVENTION

The present invention is directed toward a method of defibrillating the heart utilizing three electrodes and a novel asymmetric biphasic stimulation pulse.

The electrode system comprises a single catheter having one or more electrode areas placed at the distal end for location in the apex of the ventricle. A second set of catheter born electrodes is located outside of the atrium of the heart to reduce the possibility of generating atrial fibrillation during ventricular defibrillation. The third electrode of the system is placed subcutaneously laterally near the heart, but outside the rib cage of the patient. This electrode system may be implanted under local anesthetic, and does not require a thoracotomy or entry into the chest cavity of the patient.

Experimentation with this electrode configuration has shown a marked reduction in the amount of energy required to defibrillate the heart when used with an asymmetric biphasic stimulation pulse in comparison to the energies required to defibrillate utilizing sequential stimulation pulses at these electrode sites.

The novel defibrillation waveform is produced by the truncated discharge of a capacitor in conjunction with polarity reversal at the electrode site. This procedure produces an asymmetric biphasic pulse.

BRIEF DESCRIPTION OF THE DRAWINGS

FIG. 4 is a table comparing experimental results of the present lead system and asymmetric biphasic waveform with the prior art sequential monophasic waveform.

DETAILED DESCRIPTION OF THE ILLUSTRATIVE EMBODIMENT

The invention described herein is based upon laboratory work reported in tabular form within the description. The electrode system utilized within the heart is similar to a Medtronic ® 6880 lead which is the subject of U.S. Pat. No. 4,355,646, issued to Kallok et al, which is herein incorporated by reference.

Figure 1:
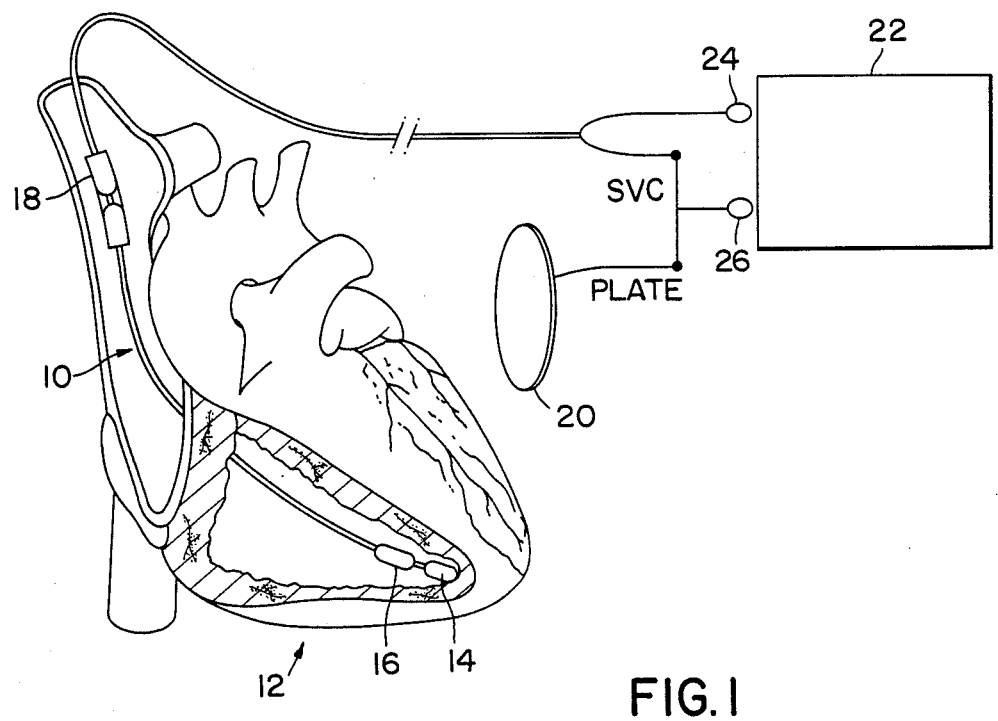
FIG. 1 is a simplified cross-section of the heart showing the location of the electrodes.

As shown in FIG. 1, a catheter 10 may be inserted into the heart generally shown as 12. A number of catheter borne electrodes are shown in the figure, and include a pacing tip 14 at the distal end of the electrode with a ring electrode 16 spaced in the ventricle. In a similar fashion, a ring electrode is shown outside of the heart at 18. The electrode system also comprises a subcutaneous disk or plate electrode shown as 20 in the figure.

In operation, the distal ring electrode is brought out through a terminal block and is electrically connected to the defibrillator 22 through a first electrode terminal 24. The subcutaneous plate electrode 20 is electrically interconnected with the proximal ring electrode 18, and they are electrically connected to the defibrillator through a second terminal 26.

Experimental laboratory work has indicated that this arrangement is preferred for defibrillating the heart, since it results in a substantial reduction in the amount of energy required to defibrillate the heart.

The table of FIG. 4 characterizes the improvement obtained with the present invention. In the experiment, the lead system was implanted as described, and defibrillation thresholds were measured using two sequential monophasic pulse waveforms and one biphasic asymmetrical pulse waveform disclosed herein. The mean defibrillation threshold for the prior art waveform was 593 volts, while defibrillation was achieved at a lower mean voltage of 549 volts for the asymmetric biphasic waveform. Most significantly, the mean stored energy required to defibrillate is only 7.7 joules with the asymmetric biphasic waveform as compared with over 18 joules with the prior art monophasic pulse waveform.

Figure 2:
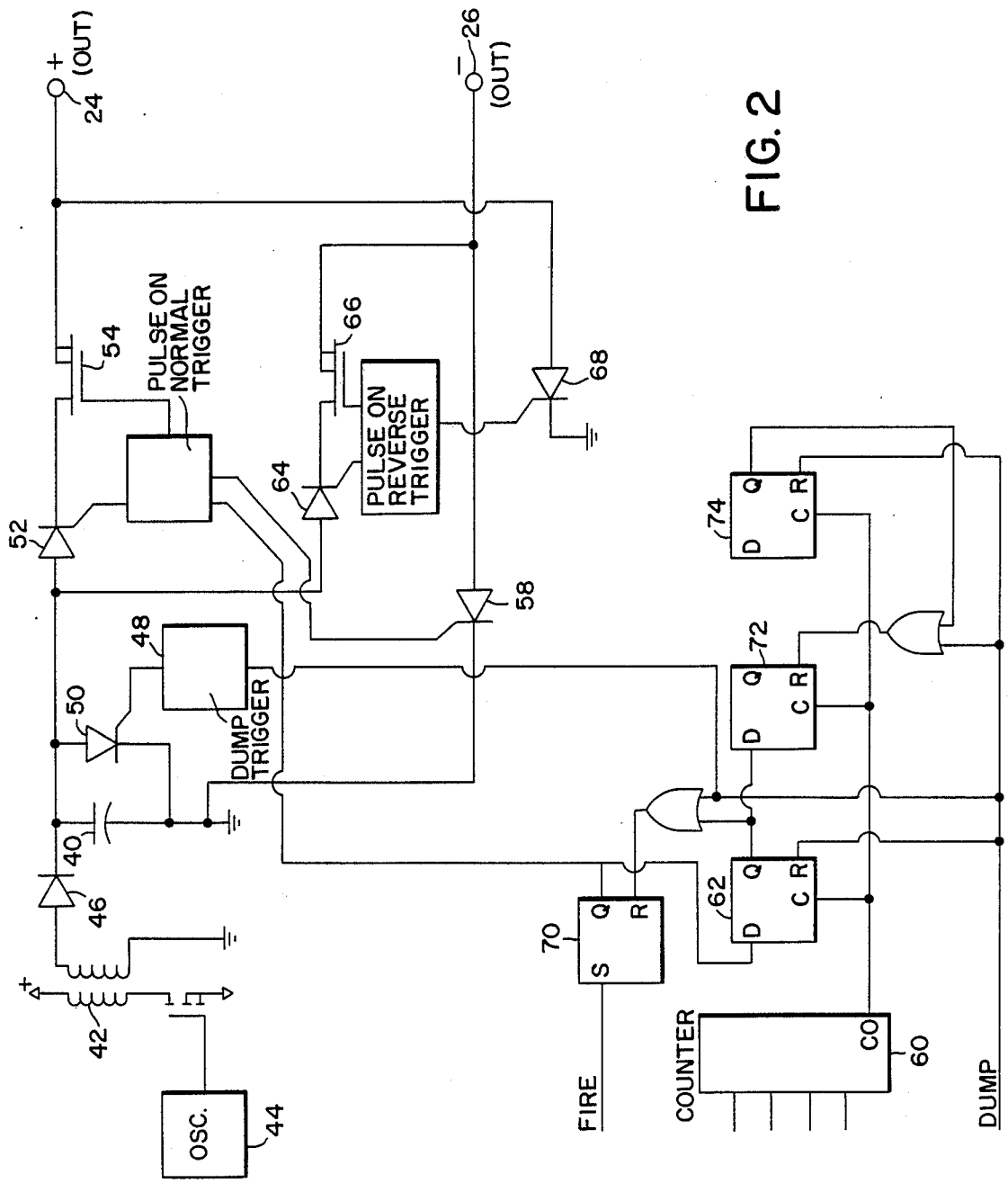
FIG. 2 is a circuit schematic for generating the asymmetric biphasic waveform of FIG. 3.

This electrode system is especially useful when utilized in conjunction with an asymmetric biphasic waveform such as that produced by the circuit of FIG. 2.

Figure 3:
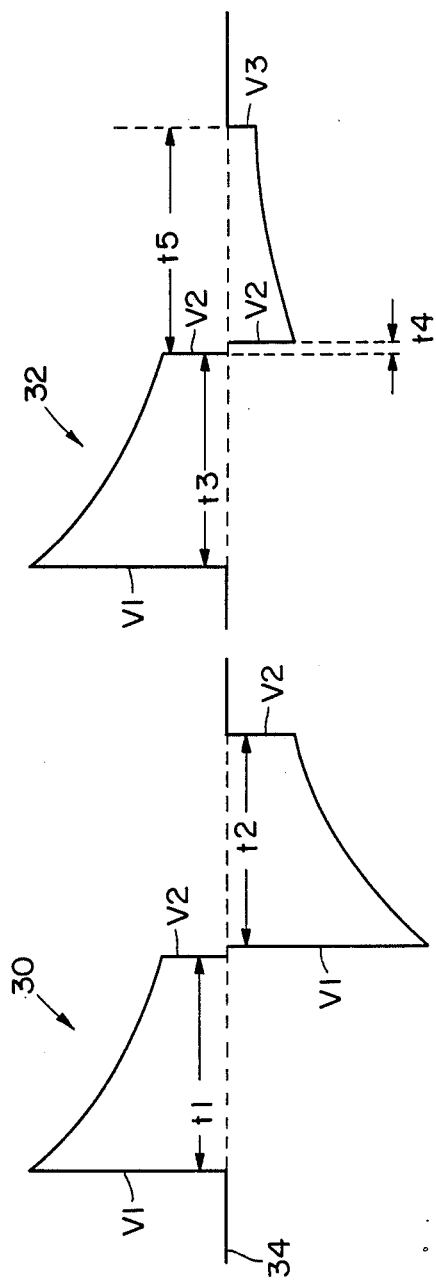
FIG. 3 is a waveform diagram showing the asymmetric biphasic stimulation waveform in comparison with a prior art biphasic waveform.

Turning to FIG. 3, there is shown a prior art waveform designated generally 30 shown in proximity to the asymmetric biphasic waveform generated by the circuitry of FIG. 2 shown generally as 32. In the prior art system, a first capacitor is coupled to an electrode system and discharged from a first voltage V1 through an electrode system representing a resistive impedance to a second lower voltage level V2. After polarity reversal, a second capacitor, which has likewise been charged to voltage V1, is discharged through the lead system to the second voltage level V2. This waveform, although efficacious, requires multiple capacitors, and results in a substantially symmetric waveform about the base line 34.

In contrast, the circuitry of FIG. 2 generates an asymmetric waveform B2 through the discharge of a single capacitor from a first voltage V1 to a second voltage V2. After polarity reversal, the electrode system continues the discharge from V2 down to a third voltage V3. As can be seen from the figure, this does not result in a symmetric waveform about the base line 36, but rather results in an unbalanced or asymmetric waveform. The experimental work performed with the asymmetric waveform involved pulse durations for each phase of the waveform (t3, t5) which were equal and varied between 4 and 5 milliseconds. In a similar fashion, the defibrillation threshold was found to correspond to a V1 voltage of between 400 and 700 volts.

The asymmetrical biphasic pulse waveform of FIG. 3 may be generated with a circuit as shown in FIG. 2, wherein the electrode system is coupled to a terminal network comprising first and second terminals (24, 26). The energy storage means may comprise one or more capacitors shown in the schematic as 40. The capacitor is charged from a transformer 42 coupled oscillator circuit 44. The oscillating voltage produced by the secondary winding of the transformer is rectified by diode 46 for storage in capacitor 40. Should discharge of capacitor 40 be required by the system, dump trigger 48 will control the gate of SCR 50 to provide a discharge path for the energy stored in capacitor 40 to ground.

When defibrillation of the heart is required, detection circuitry (not shown) generates a first input on the set input of flip-flop 70. The Q output turns on SCR 52 and SCR 58 and FET 54 initiating the leading edge V1 of the output waveform 32 between terminals 24 and 26. Counter preset input applied to counter 60 determines the t3 time duration of waveform 32. When the counter 60 times out, the carry out signal sets flip-flop 62 which resets flip-flop 70. This operation terminates the t3 time period.

The counter 60 is then preset to time out the t4 separation period. Upon time out, the carry out signal of the counter 60 sets the Q output of flip-flop 72 which turns on SCR 64, FET 66 and SCR 68.

The counter is next preset to time out the t5 pulse duration period. When the counter times out the t5 period, the carry out signal of the counter sets the Q output flip-flop 74, thus resetting flip-flop 72, and thus terminating the t5 period of the pulse waveform 32.

At the conclusion of this timing cycle, the charge oscillator may begin to recharge the energy storage capacitor 40 as previously described in preparation for the next defibrillation pulse if additional defibrillation shocks are required.

What is claimed is:

1. A method of applying electrical energy to a human heart, comprising:
   implanting a first electrode having a first terminal within the ventricle of said heart;
   implanting a second electrode adjacent the exterior of said heart;
   implanting a third electrode remote from said heart;
   electrically interconnecting said second and third electrodes, forming an electrode pair having a second terminal; and
   discharging a capacitor between aid first and second terminals for a first predetermined time period, followed by reversing the polarity of said capacitor with respect to said first and second terminals, then discharging said capacitor between said first and second terminals for a second predetermined time period, forming an asymmetrical biphasic pulse waveform.

2. A method of applying electrical energy to a human heart, comprising:
   positioning multiple electrodes about said heart;
   interconnecting said electrodes to crate a two terminal network, comprising a first and second terminal; and
   discharging a capacitor between said first and second terminals for a first predetermined time period, followed by reversing the polarity of said capacitor with respect to said first and second terminals, then discharging said capacitor between said first and second terminals for a second predetermined time period, forming an asymmetrical biphasic pulse waveform.

3. A method of applying electrical energy to a human heart, comprising:
   positioning at least three electrodes around said heart;
   interconnecting said electrodes to create a two terminal network, comprising a first and second terminal; and
   discharging a capacitor between said first and second terminals for a first predetermined time period, followed by reversing the polarity of said capacitor with respect to said first and second terminals, then discharging said capacitor between said first and second terminals for a second predetermined time period, forming an asymmetrical biphasic pulse waveform.

4. The method of claim 3 further comprising:
   detecting ventricular tachycardia or fibrillation; and
   discharging said capacitor following detection of ventricular fibrillation or tachycardia.

5. The method of claim 1 wherein said implanting steps further comprise:
   implanting said second electrode in the superior vena cava of the heart; and
   implanting said third electrode subcutaneously outside the chest cavity.

6. The method of claim 5 further comprising:
   detecting ventricular tachycardia or fibrillation; and
   discharging said capacitor following detection of ventricular fibrillation or tachycardia.

7. The method of claim 1 further comprising:
   detecting ventricular tachycardia or fibrillation; and
   discharging said capacitor following detection of ventricular fibrillation or tachycardia.

8. Apparatus for generating and delivering biphasic electrical shocks to the heart of a patient to restore normal cardiac rhythm comprising:
   means for positioning at least three implantable electrodes spaced in and around said heart;
   means for interconnecting said electrodes into a two terminal network comprising first and second electrode terminals; and
   pulse generator means for generating a biphasic shock across said first and second electrode terminals further comprising:
   capacitor storage means having first and second output terminals;
   means for charging said capacitor storage means to a predetermined voltage; and
   means for successively discharging said capacitor storage means between said first and second electrode terminals for first and second time periods comprising means for coupling said first and second output terminals to said first and second electrode terminals, respectively, during said first time period and to said second and first electrode terminals, respectively, during said second time period, thereby applying a biphasic shock through said electrodes to said heart.

9. The apparatus as claimed in claim 1 wherein said means for positioning at least three electrodes spaced in and around said heart further comprises:
   means for positioning a first electrode in the right ventricle of said heart;
   means for positioning a second electrode in the region of said patient's superior vena cava;
   means for positioning a patch electrode subcutaneously outside the thoracic cavity of said patient; and
   first electrical conducting means for electrically connecting said first electrode with one of said first and second electrode terminals and second electrical conducting means for electrically connecting both said second electrode and said subcutaneous patch electrode with the other of said first and second electrode terminals.

10. The apparatus as claimed in claim 8 wherein said means for positioning at least three electrodes spaced in and around said heart further comprises:
    an intravasclar catheter insertable within the heart of said patient having a first electrode located near the distal end of said catheter for positioning in the right ventricle and a second electrode carried on said catheter at a distance from said first electrode for positioning in the superior vena cava region;
    a subcutaneous patch electrode electrically connected with said second electrode of the intravascular catheter for positioning subcutaneously outside the thoracic cavity of the patient; and
    first electrical conducting means for electrically connecting said first electrode with one of said first and second electrode terminals and second electrical conducting means for electrically connecting both said second electrode and said subcutaneous patch electrode with the other of said first and second electrode terminals.

11. The apparatus as claimed in claim 10 wherein said pulse generator means further comprises:
    means for detecting an arrhythmic condition of the heart; and
    means for discharging said capacitor storage means upon detection of an arrhythmic condition by said detection means.

12. The apparatus as claimed in claim 8 wherein said pulse generator means further comprises:
    means for detecting an arrhythmic condition f the heart; and
    means for discharging said capacitor storage means upon detection of an arrhythmic condition by said detection means.

* * * * *

UNITED STATES PATENT AND TRADEMARK OFFICE
CERTIFICATE OF CORRECTION

PATENT NO. : 4,953,551
DATED : September 4, 1990
INVENTOR(S) : Rahul Mehra, and William Combs

It is certified that error appears in the above-indentified patent and that said Letters Patent is hereby corrected as shown below:

Column 4, Line 60, delete "aid", and insert in its place --said--.

Column 6, Line 11, delete "claim 1", and insert in its place --claim 8--.

Column 6, Line 57, delete "f", and insert in its place --of--.

Signed and Sealed this

Twenty-seventh Day of September, 1994

Attest:

BRUCE LEHMAN

Attesting Officer

Commissioner of Patents and Trademarks